United States Patent
Awang et al.

(10) Patent No.: US 8,178,714 B2
(45) Date of Patent: May 15, 2012

(54) METHOD TO PRODUCE POLYHYDROXY CARBOXYLIC ACID ESTERS OF POLYETHYLENE GLYCOL

(75) Inventors: Roila Awang, Selangor (MY); Aminah Nor Azizan, Selangor (MY); Salmiah Ahmad, Selangor (MY)

(73) Assignee: Malaysian Palm Oil Board, Kuala Lumpur (MY)

( * ) Notice: Subject to any disclaimer, the term of this patent is extended or adjusted under 35 U.S.C. 154(b) by 301 days.

(21) Appl. No.: 12/358,361

(22) Filed: Jan. 23, 2009

(65) Prior Publication Data

US 2009/0192329 A1   Jul. 30, 2009

(30) Foreign Application Priority Data

Jan. 25, 2008   (MY) .................. PI20080137

(51) Int. Cl.
*C07C 69/527* (2006.01)
(52) U.S. Cl. ........ 560/224; 554/166; 554/213; 514/844; 514/846; 514/881
(58) Field of Classification Search ........................ None
See application file for complete search history.

(56) References Cited

U.S. PATENT DOCUMENTS

| | | | | |
|---|---|---|---|---|
| 2,528,136 A * | 10/1950 | Goldstein et al. | ................ | 516/74 |
| 2,652,410 A * | 9/1953 | Cunningham et al. | ........ | 554/121 |
| 3,669,848 A | 6/1972 | Seiden | | |
| 5,675,032 A | 10/1997 | Heuer et al. | | |
| 6,723,863 B2 | 4/2004 | Lee et al. | | |
| 2005/0159610 A1 | 7/2005 | Poppe | | |
| 2006/0041158 A1* | 2/2006 | Albers et al. | ................ | 554/174 |

FOREIGN PATENT DOCUMENTS

| | | |
|---|---|---|
| EP | 1681281 | 7/2006 |
| JP | 2005-132794 | * 5/2005 |
| WO | WO2007038025 | 4/2007 |

OTHER PUBLICATIONS

Oya, et al., W/O/W Type Emulsion comositoin, 2005, JP 2005-132794, English translation.*
Carothers, W., Polymerization, 1931, Chemical Reviews, 8(3), pp. 353-426 (74 pages).*
Walton, L.L., Poly(oxyethylene) fatty acid esters, 1962, American Perfumer adn Cosmetics, 77, No. 10, (1 page abstract).*

* cited by examiner

*Primary Examiner* — Yate K Cutliff
(74) *Attorney, Agent, or Firm* — Preston Smirman; Smirman IP Law, PLLC

(57) ABSTRACT

A method to produce polyethylene glycol ester comprises the step of reacting polyethylene glycols with polyhydroxy carboxylic acids or estolides polyhydroxy fatty acids at a temperature of 120° C. to 200° C. in the absence of any catalysts.

5 Claims, 1 Drawing Sheet

METHOD TO PRODUCE POLYHYDROXY CARBOXYLIC ACID ESTERS OF POLYETHYLENE GLYCOL

FIELD OF THE INVENTION

The present invention relates to a method to produce hydroxy fatty ester of polyethylene glycol which can be used as emulsifier, wetting agent or surfactant in cosmetic composition. In more particular, the disclosed method utilizes the unique molecular structure of the raw material, hydroxy fatty acids, to perform a catalyst-free esterification process.

BACKGROUND OF THE INVENTION

Polyethylene glycol ester is a mono or diester of a fatty acid or oil reacted with a polyethylene glycol. It has been widely used as emulsifiers, pearlizers, stabilizers, solublizers or viscosity-controlling agent especially in household and cosmetic products such as lotion, cream, hand soap, shampoo and so on. Owing to its versatility in different filed of application, numerous effort has been contributed to improve the existing polyethylene glycol ester types or devise a new types of polyethylene glycol ester derivatives with improved properties. Furthermore, improvement also been made to enhance the rate, selectivity, or efficiency of the esterification reaction.

Patent Publication no WO2007038025 filed an application on an improved process which able to produce high purity of polyol monoester. This application claims that pre-heating of the polyols before reacting with the fatty acid or its derivatives can attain the purpose of producing high fraction of polyol monoester. In the disclosed examples, sodium methoxide is employed as the catalysts to enhance the reaction.

Lee et.al. have filed a U.S. Pat. No. 6,723,863 regarding a method for tranesterification of polyols and fatty acids in the absence of oxygen. Such approach claims to be effective in avoiding unnecessary oxidation of the reaction product.

Another United State patent with publication no. 2005159610 discloses a process to produce polyol esters which is light in colour by end of the process without requiring further distillation or de-colouring. Particularly, the fatty acid C1 to C5 alkyl esters are reacted with polyols in the presence of catalysts and borohydride in which sodium methoxide is employed as the catalysts.

U.S. Pat. No. 3,669,848 relates to a method to produce propylene glycol monoester with low fraction of diester product by conducting the reaction in vacuum distillation between the temperature of 170° C. to 285° C. under negative pressure.

European patent with publication no. 1681281 claims a method of producing fatty acid monoesters by means of esterification between alcohol and a compound that is selected from a fat of animal origin, a fat of vegetable origin, and a fatty acid methyl ester. This invention employs basic solid catalysts which are monovalent or polyvalent metal oxides as the catalysts to enhance the reaction. With the aid of solid catalysts, the problems like presence of catalysts residues in the end products can be prevented.

U.S. Pat. No. 5,675,032 discloses a process for preparation of polyethylene glycol di (2-(4-chloro-2-methylphenoxy)-propionic acid ester mixtures by reaction between 2-(4-chloro-2-methylphenoxy)-propionic acid and a mixture of different types of polyethylene glycol. Along the reaction of this invention no catalyst employed.

Most of the processes now available for the production of polyethylene glycol ester or its derivatives are mainly employed strong acids or bases as the catalysts which may render the process uncontrollable due to the drastic condition applied. Over oxidation is common in such condition that lead to production of different unwanted side products thus affect the quality of the end products derives thereof. Moreover, tedious processes are required to get rid of the catalysts residues in the produced polyethylene glycol by end of the esterification because presence of catalysts residue in the polyethylene glycol ester produced is detrimental to the end product derives thereof. In the esterification processes, it is found impractical to reuse the catalysts too as the homogenous catalysts used is impossible to be extracted intact from a pool of polyethylene glycol ester produced while heterogenous catalysts are normally degraded due to the drastic condition after the process. Therefore, it is ideal to the esterification process progress smoothly without the need of drastic condition to enhance the rate of the reaction, specifically a self-initiated reaction under suitable condition without the use of catalysts.

SUMMARY OF THE INVENTION

It is an object of the present invention to disclose a catalysts-free process for esterifying polyols with polyhydroxy carboxylic acids which the rate of reaction would not be affected by the absence of the use of catalysts.

Further object of the present invention is to provide a time-saving process. In more particular, the process disclosed in the present invention does not require additional purifying steps to remove catalyst residues in the produced polyethylene glycol ester in opposed to other common processes.

Another object of the present invention aims to offer a process which is less costly as no catalysts required to be used in the disclosed process and labouring cost of the disclosed process also greatly reduced with less processing steps.

Still another object of the present invention is to disclose an composition which can be obtained by the disclosed process. This composition possess excellent chemical properties that made this composition suitable to be applied as emulsifiers, solublizers, wetting agent or solublizers for cosmetic or household products. At least one of the preceding objects is met, in whole or in part, by the present invention, in which one of the embodiment of the present invention a method to produce polyethylene glycol ester comprises the step of reacting polyethylene glycols with polyhydroxy carboxylic acids or estolides of polyhydroxy fatty acids at a temperature of 120° C. to 200° C. in the absence of any catalysts.

According to one of the preferred embodiment, the polyhydroxy carboxylic acids used in the present invention preferably have at least two hydroxy groups located on two neighbouring carbon atoms. It is most preferred that the polyhydroxy carboxylic acids are polyhydroxy fatty acids which can be plant or animal sources derived or processed derivatives from the mentioned sources. It is most preferred that the polyhydroxy fatty acids are 9,10-dihydroxystearic acid (DHSA).

In order to carry out the preferred embodiment of the present invention, the polyhydroxy carboxylic acids preferably have a carbon chain of 18 carbon atoms to acquire the desired products, while the polyethylene glycol ester is preferably having an average molecular weight of 200 to 2000.

Preferably, the polyethylene glycols and the polyhydroxy fatty acids are in a molar ratio of 1-3 to 1-5. Nonetheless, in order to produce higher ratio of monoester, excess glycol is required. On the other hand, for producing higher ratio of diester in product mixture, excess fatty acid is required.

A cosmetic liquid composition comprises dihydroxy stearic fatty acid-polyethylene glycol esters as emulsifier.

DETAILED DESCRIPTION OF THE INVENTION

The present disclosure includes as contained in the appended claims, as well as that of the description hereinafter. Although this invention has been described in its preferred form with a degree of particularity, it is understood that the present disclosure of the preferred form has been made only by way of example and that numerous changes in the details of the invention may be resorted to without departing from the scope of the invention.

The present invention is a method to produce polyethylene glycol ester comprises the step of reacting polyethylene glycols with polyhydroxy carboxylic acids or estolides of polyhydroxy fatty acids at a temperature of 120° C. to 200° C. in the absence of any catalysts. It is most preferable that the carboxylic acids employed in the process are fatty acids. It was found by the inventors of the present invention that polyhydroxy carboxylic acids, more preferred polyhydroxy fatty acids, or estolides of polyhydroxy fatty acids can be actively react with polyethylene glycol and the like compounds in a heated environment without the aid of catalysts. It is important to be noted that scope of the present invention should not be limited though the actual mechanisms to illustrate the progress of the reaction is yet determined. Nevertheless, the reactivity of the reaction possibly can be attributed to the polyhydroxy groups available on the carbon chain of the polyhydroxy carboxylic acids or the estolides of polyhydroxy fatty acids. Owing to the additional hydroxy groups on the reactants, the molecules have higher polarity.

Figure 1:
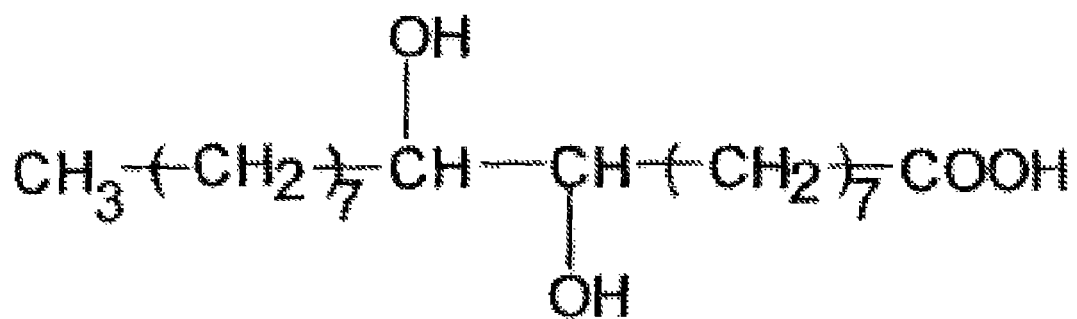
FIG. 1 shows the chemical structure of the carboxylic acids used in one of the preferred embodiments of the present invention.
Figure 2:
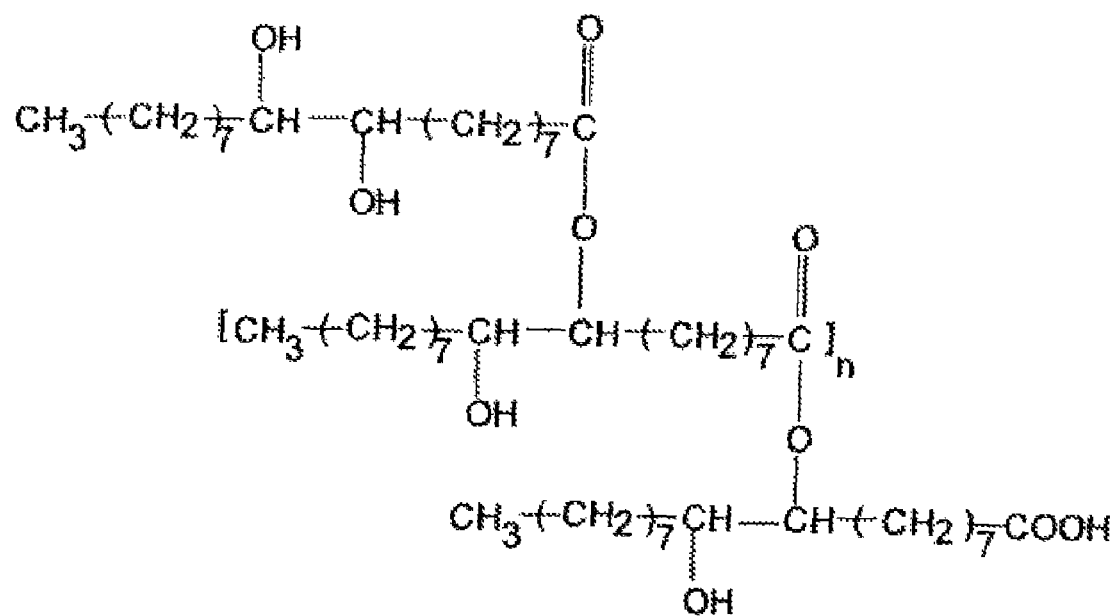
FIG. 2 shows the chemical structure of the DHSA estolides which can be used to carry out the present invention.

In accordance with the preferred embodiment, the polyhydroxy carboxylic acids or polyhydroxy fatty acids or the estolides of polyhydroxy fatty acids have at least two hydroxy groups located on two neighbouring carbon atoms. As in the foregoing description, the inventors of the present invention found that the two or more hydroxy groups located on two neighbouring carbon atoms shows satisfying reactivity in the tranesterification process in the absence of the catalysts. For example, the molecule structures as shown in FIG. 1, 9,10-dihydroxystearic acid (DHSA), and FIG. 2, DHSA-estolide are employed in the preferred embodiment of the disclosed process. In fact, the polyhydroxy carboxylic acids or polyhydroxy fatty acids or the estolides of polyhydroxy fatty acids used in the disclosed process are of natural sources or derivatives derived thereof such as plant oil and animal fats from soybean oil, linseed oil, corn oil, sunflower oil, canola oil, rapseed oil, coconut oil, palm kernel oil, palm oil, cotton oil, peanut oil, olive oil, tall oil, safflower oil, lard, tallow, and cod liver oil. Yet the hydroxyl groups presented in the alkyl chain are not affected or modified by the end of the esterification process, where transmittance peak of hydroxyl group still can be observed at ~3300 $cm^{-1}$ wavenumber in FTIR spectrum. It is important to be noted that utilization of the polyhydroxy carboxylic acids or polyhydroxy fatty acids or the estolides of polyhydroxy fatty acids not only provides the required reactivity the esterification reaction, but also yield polyethylene glycol esters with the desired quality such as extremely low in acidic value. With such properties, the polyethylene glycol ester produced is ideal for preparation of cosmetic and household products. Moreover, the presence of hydroxyl group provide hydrophilic properties when compared to ordinary PEG ester such as PEG stearate. It could theoretically impart structure to creams and lotions and could be employed as main or secondary emulsifiers.

Further embodiment of the present invention, the polyhydroxy carboxylic acids or polyhydroxy fatty acids or the estolides of polyhydroxy fatty acids preferably have a carbon chain of 18 carbon atoms, but not limited to, to obtain the polyethylene glycol ester with desired properties. One skilled in the art shall appreciate the fact that the length of the carbon chain is crucial in determining the solubility and polarity of the polyethylene glycol ester produced thus affect its applicability in different products. Therefore, any modification thereof shall not depart from the scope of the present invention.

Likewise, the polyethylene glycols employed preferably has an average molecular weight of 200 to 2000 to produce the polyethylene glycol ester with the desired molecular weight. The lower molecular weight esters are lipophilic and soluble in oil or non-aqueous systems, such lipophilic ester may have a molecular weight ranged from about 200 to 400 which mainly used for influence stability, viscosity, wetting, foaming and the like properties in an incorporated composition. On the other hand, those polyethylene glycol ester produced with molecular weight ranges from 500 to 1450 are mostly used for emulsification. Therefore, it is conceivable to one skilled in the art to arrange reaction between the polyhydroxy carboxylic acids and polyethylene glycols in different molecular weight to acquire the esters with specific molecular weight by the disclosed reaction.

Moreover, the polyethylene glycols and the polyhydroxy fatty acids are preferably to have a molar ratio of 1-3 to 1-5. Yet, excess glycol is required in order to produce higher ratio of monoester, while excess fatty acid is required for producing higher ratio of diester in product mixture.

In the present invention, it was found that the ratio of the reactants are of important in determining the fraction of the end products. Specifically, the amount of monoester to diester and other side products are relatively affected by the initial ratio of the reactants. Furthermore, the acidic value of the ester produced in the disclosed process is determined by relative initial amount of the reactants too. Greater molar of polyethylene glycol to the polyhydroxy carboxylic acids or polyhydroxy estolides tends to produce polyethylene glycol ester with lower acidic value which is desirable.

While not essential to perform the disclosed process, the environment for conducting the reaction is preferably to be inert to the reactants. To attain such requirement, the reactor for carrying out the esterification may be vacuumed or charged with inert gases like carbon dioxide or nitrogen. Low concentration of oxygen or most preferred absence of oxygen in the reaction environment is favoured in reducing the production of unwanted side products.

According to the most preferred embodiment, a toiletry composition comprises dihydroxy stearic fatty acid-polyethylene glycol esters as surfactant or emulsifiers is disclosed. As shown in the examples below, the disclosed toiletry compositions incorporated with polyhyrdoxy carboxylic acid-polyethylene glycol ester have excellent wetting and dirt removing effect.

The following example is intended to further illustrate the invention, without any intent for the invention to be limited to the specific embodiments described therein.

EXAMPLE 1

31.65 g of DHSA was placed in a reaction flask equipped with a magnetic stirrer, a thermometer, a nitrogen gas inlet and a condenser. Depending on the mole ratio and average molecular weight, a sufficient amount of polyethylene glycol was added. The mixture was heated in an oil bath at various reaction temperatures under $N_2$ atmosphere with continuous stirring. The water, which produced during the reaction, was distilled off. The reaction was monitored by measuring the acid value. Table 1 shows the acid value for the esterification of DHSA and PEG 200 at mole ratio of 1:1.

TABLE 1

| Temperature, ° C. | Acid Value, mgKOH/g |
|---|---|
| 120 | 64.40 |
| 150 | 57.45 |
| 170 | 36.87 |
| 180 | 16.84 |

EXAMPLE 2

Example 1 was repeated. Instead of variable reaction time, the reactions were carried out at different mole ratio for about 2-5 h.

TABLE 2

| Mole ratio (DHSA:PEG 200) | Acid Value, mgKOH/g |
|---|---|
| 2:1 | 28.19 |
| 1:1 | 16.87 |
| 1:1.5 | 7.28 |
| 1:2 | 2.32 |
| 1:5 | 1.73 |

EXAMPLE 3

Example 1 was repeated. In this experiment PEG with various average molecular weight was used as a feedstock. The reaction was carried out at 170° C. Mole ratio of DHSA to PEG is 1:1

TABLE 3

| PEG | Acid Value, mgKOH/g |
|---|---|
| PEG200 | 26.84 |
| PEG300 | 24.56 |
| PEG1500 | 16.36 |
| PEG2000 | 12.58 |

EXAMPLE 4

The same procedure was followed as in Example 1, except that DHSA-estolides were used as acyl donors. The reaction mixture was carried out at 170° C. for 2-3 h. Mole ratio of DHSA-estolide to PEG 200=1:1

TABLE 4

| DHSA-estolide | Acid Value, mgKOH/g |
|---|---|
| Diestolide | 9.80 |
| Triestolide | 8.61 |

EXAMPLE 5

Use of PEG-DHSA ester and PEG-DHSA estolide ester as a wetting agent

TABLE 5

| PEG esters | Wetting time, sec |
|---|---|
| DHSA-PEG200 | 27 |
| DHSA-PEG300 | 17 |
| Diestolide-PEG200 | 48 |
| Triestolide-PEG200 | 88 |

0.1% (w/v) of the samples in deionized water was prepared in different containers. Patches of unsoiled cloth were cut and placed onto each solution solution. The wetting power was the time taken by the patches to fully sink to the bottom of the containers.

EXAMPLE 6

Use of DHSA-PEG200 as an Emulsifier in O/W Emulsion System.

Emulsion test of the samples were carried out as follows:
75 parts of water phase and 5 parts of sample were placed in a beaker. Under sufficient agitation, 20 parts of oil phase was added. The mixture was mixed for additional 5 minutes. After this time, the mixture was observed after 24 h and 7 days storage at room temperature.

TABLE 6

| | Estimation of Emulsion = 100 × Emulsion Layer/Total Layer | |
|---|---|---|
| Oil Phase | 24 h | 7 days |
| Dimethicone | 100 | 100 |
| Mineral Oil | 100 | 100 |
| Isopropyl Myristate | 100 | 100 |
| MCT | 100 | 100 |
| RBD Palm Kernel Oil | 100 | 100 |

MCT = medium chain triglycerides

EXAMPLE 7

Use of PEG Ester as a Soil Remover

The detergency of the PEG ester (0.1% solution) in various water hardness at room temperature was tested on soiled cloth, AS9

TABLE 7

| | Water Hardness, ppm | | |
|---|---|---|---|
| Sample | 50 | 150 | 350 |
| DHSA-PEG200 | 21.63 | 18.06 | 16.92 |
| DHSA-PEG300 | 20.75 | 19.29 | 18.41 |
| Diestolide-PEG200 | 23.69 | 20.77 | 21.28 |
| Triestolide-PEG200 | 10.53 | 6.60 | 5.88 |

It is to be understood that the present invention may be embodied in other specific forms and is not limited to the sole embodiment described above. However modification and equivalents of the disclosed concepts such as those which readily occur to one skilled in the art are intended to be included within the scope of the claims which are appended thereto.

The invention claimed is:

1. A method to produce polyethylene glycol ester comprises the step of reacting polyethylene glycols with polyhydroxy fatty acids or estolides of polyhydroxy fatty acids at a temperature of 120° C. to 200° C. in the absence of any catalysts, wherein the polyhydroxy fatty acids have at least two hydroxy groups located on two neighbouring carbon atoms.

2. The method according to claim 1, wherein the polyhydroxy fatty acids have a carbon chain of 18 carbon atoms.

3. The method according to claim 1, wherein the polyethylene glycols have an average molecular weight of 200 to 2000.

4. The method according to claim 1, wherein the polyethylene glycols and the polyhydroxy fatty acids has a molar ratio of 1-3 to 1-5.

5. The method according to claim 1, wherein the polyhydroxy fatty acids are 9, 10-dihydroxystearic acid.

* * * * *